(12) United States Patent
Koullick et al.

(10) Patent No.: US 7,582,068 B2
(45) Date of Patent: Sep. 1, 2009

(54) OCCLUSION RESISTANT HYDROCEPHALIC SHUNT

(75) Inventors: Edouard Koullick, Golden Valley, MN (US); Marc Hendriks, Brunssum (NL); William Bertrand, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 201 days.

(21) Appl. No.: 10/781,568

(22) Filed: Feb. 18, 2004

(65) Prior Publication Data

US 2004/0220510 A1   Nov. 4, 2004

(51) Int. Cl.
*A61M 5/00* (2006.01)
*A61F 2/06* (2006.01)

(52) U.S. Cl. .................. 604/8; 604/9; 604/264; 623/1.42

(58) Field of Classification Search ........... 604/7–10, 604/264, 266; 623/1.42, 1.43, 1.45, 1.46; 424/422–425
See application file for complete search history.

(56) References Cited

U.S. PATENT DOCUMENTS

| | | | | |
|---|---|---|---|---|
| 4,655,645 A | 4/1987 | Hipkins, Sr. et al. | ........ | 405/261 |
| 5,282,844 A | 2/1994 | Stokes et al. | ................ | 607/120 |
| 5,707,366 A * | 1/1998 | Solomon et al. | ............ | 604/265 |
| 5,928,182 A * | 7/1999 | Kraus et al. | ..................... | 604/9 |
| 6,013,155 A | 1/2000 | McMillin et al. | ............ | 156/345 |
| 6,110,155 A * | 8/2000 | Baudino | ...................... | 604/265 |
| 6,214,370 B1 | 4/2001 | Nelson et al. | ............... | 424/425 |
| 6,248,129 B1 | 6/2001 | Froix | ........................ | 623/1.42 |
| 6,348,042 B1 | 2/2002 | Warren, Jr. | ..................... | 604/8 |
| 6,652,581 B1 | 11/2003 | Ding | ........................ | 623/1.39 |
| 6,656,506 B1 * | 12/2003 | Wu et al. | ..................... | 424/489 |
| 6,663,881 B2 * | 12/2003 | Kunz et al. | ..................... | 424/423 |
| 7,008,397 B2 * | 3/2006 | Tweden et al. | ................. | 604/8 |
| 7,077,859 B2 * | 7/2006 | Sirhan et al. | ............... | 623/1.15 |
| 7,195,608 B2 * | 3/2007 | Burnett | ......................... | 604/9 |
| 2002/0138048 A1 | 9/2002 | Tuch | | |
| 2004/0067301 A1 | 4/2004 | Ding | | |
| 2004/0147871 A1 * | 7/2004 | Burnett | ....................... | 604/9 |
| 2005/0008095 A1 * | 1/2005 | Rush et al. | .................. | 375/296 |
| 2007/0071789 A1 * | 3/2007 | Pantelidis et al. | ........... | 424/423 |

FOREIGN PATENT DOCUMENTS

| | | |
|---|---|---|
| EP | 0691130 A1 | 1/1996 |
| WO | WO 94/25081 | 11/1994 |
| WO | WO 97/04819 | 2/1997 |
| WO | WO 03/057218 | 7/2003 |
| WO | WO 2004/000383 | 12/2003 |
| WO | WO2004/073768 | 9/2004 |

\* cited by examiner

*Primary Examiner*—Leslie R Deak
(74) *Attorney, Agent, or Firm*—Kenneth Collier

(57) ABSTRACT

An occlusion resistant medical shunt, particularly a hydrocephalic shunt, is provided for implantation into a mammal. The shunt has an elongate wall structure configured as a tube having a lumen therethrough and a proximal end for receipt of bodily fluids. The bodily fluids, such as cerebrospinal fluid, flows through the shunt to a distal end for discharge of the bodily fluids. The wall structure of the shunt generally includes a biocompatible medical device material. The shunts of the present invention further include one or more occlusion resistant materials to resist occlusion of the lumenal passage in the shunt.

60 Claims, 12 Drawing Sheets

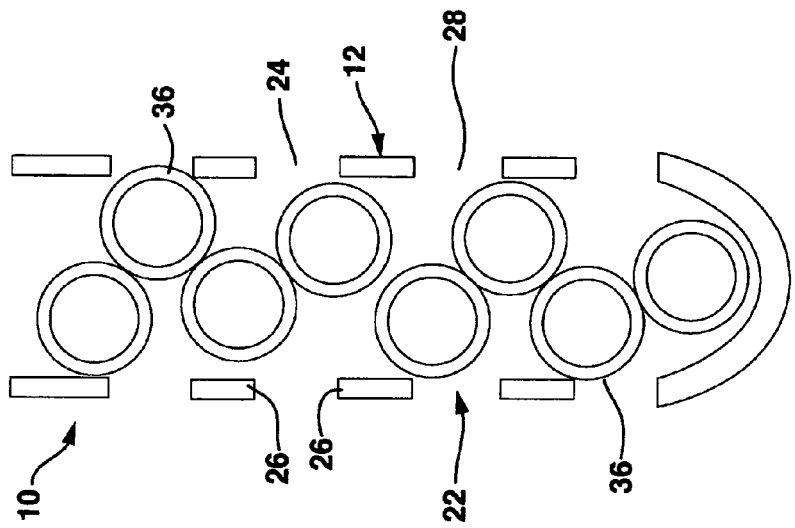
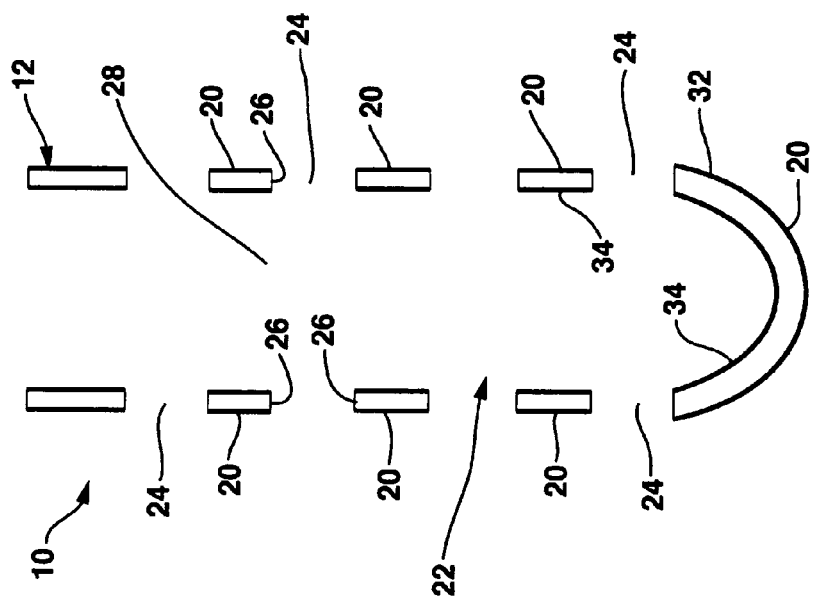

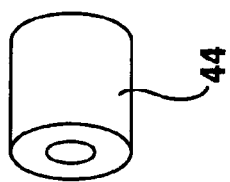
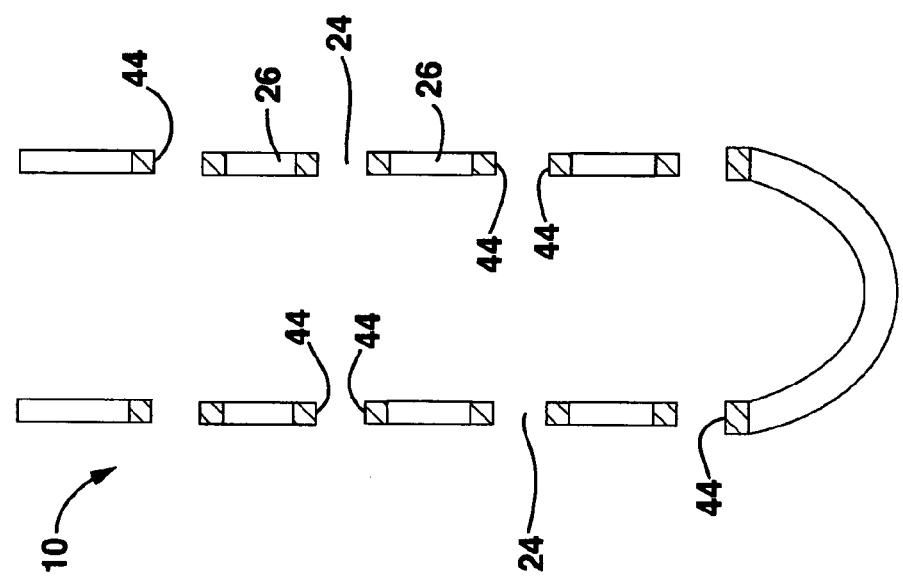

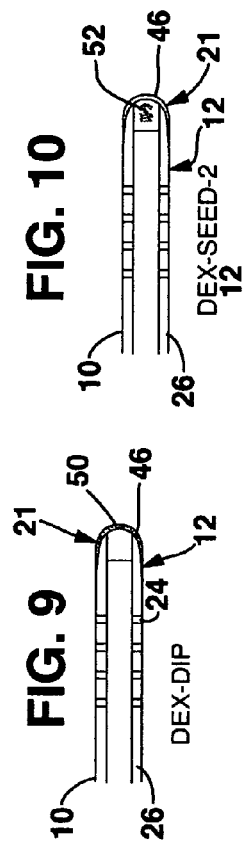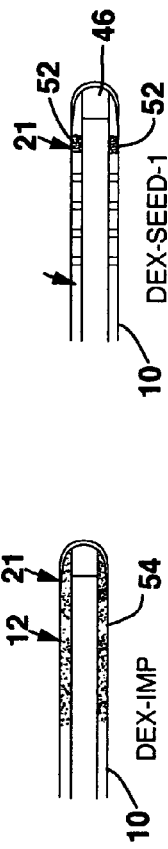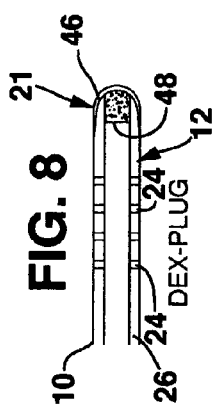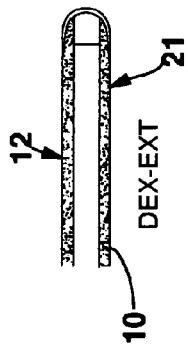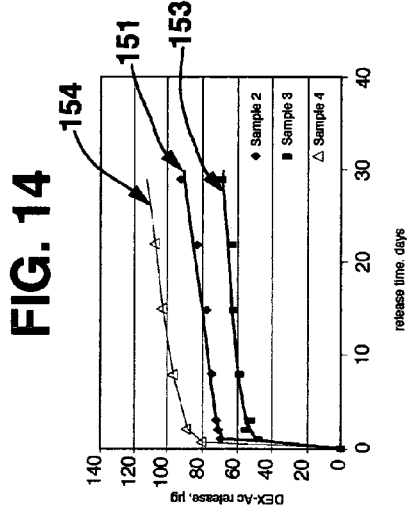

In-vitro release of RAPA from silicone catheters of different sizes.

OCCLUSION RESISTANT HYDROCEPHALIC SHUNT

FIELD OF THE INVENTION

This invention relates to cerebrospinal fluid shunts and techniques to prevent blockage or occlusion of such a shunt.

BACKGROUND OF THE INVENTION

Hydrocephalic shunts are designed to remove excess fluid from the ventricular region of the brain to a different internal location, such as the peritoneal cavity. Alternatively, cerebral spinal fluid (CSF) shunts may have a proximal end placed into the patient's ventricular region and a distal end being connected external of the patient. In either configuration, a common problem involves the immune response of the patient or inflammatory response to the insertion of the foreign body, i.e., the catheter, therein. Additionally, occlusion of the catheter lumens often occur and preclude effective drainage of the CSF fluid. It is estimated that 40% of implanted hydrocephalic shunts fail after 5 years due to tissue proliferation into the shunt lumen.

U.S. Pat. No. 6,110,155, issued to Baudino, and commonly owned by Applicant of the present application, shows an anti-inflammatory agent loaded catheter distal tip and method for preventing tissue fibrosis. The device and method utilizes, in one embodiment, dexamethasone sodium phosphate agent on a ventricular catheter tip to prevent encapsulation of the catheter. U.S. Pat. No. 6,348,042 B1, issued to Warren, Jr., discloses a bio-active shunt device and method by which the interior lumen surface of a shunt is coated with a matrix forming system having at least one enzyme configured for inciting activity to preclude the growth of obstructing cellular material. In one embodiment, the interior surface of the catheter lumen is impregnated with proteases or a matrix containing proteases that is impregnated onto the wall of the lumen to degrade cellular material including cells of the choroid plexus and peritoneum. U.S. Pat. No. 4,655,645, issued to Corbett, discloses a mechanical method and technique for preventing ingrowth into a ventricular catheter by brain tissue, e.g., the choroid plexus.

U.S. Pat. No. 5,282,844, issued to Stokes, et al., and also commonly owned by Applicant of the present invention, discloses use of steroid eluting pacing lead electrodes for cardiology applications. Other references are known to discuss a range of drug eluting devices, including stents designed to contact tissue with fully coated drug eluding surfaces. All of these references fail to disclose the novel and non-obvious combinations as disclosed herein.

BRIEF SUMMARY OF THE INVENTION

An occlusion resistant medical shunt, particularly a hydrocephalic shunt, is provided for implantation into a mammal. The shunt has an elongate wall structure configured as a tube having a lumen therethrough and a proximal end for receipt of bodily fluids. The bodily fluids, such as cerebrospinal fluid, flows through the shunt to a distal end for discharge of the bodily fluids. The wall structure of the shunt generally includes a biocompatible medical device material. The shunts of the present invention further include one or more occlusion resistant materials to resist occlusion of the lumenal passage in the shunt.

A fully implanted medical shunt for use as a hydrocephalus shunting device has a construction which controls the immunologic response that the recipient may experience after receipt of the shunt within the recipient's body. In various embodiments of the present invention, the shunt comprises an elongate wall structure configured as a tube having a lumen therethrough and a proximal end for receipt of bodily fluids and a distal end for discharge of said bodily fluids into another portion of the recipient's body. In one embodiment, the proximal end is located in the ventricular region of the brain and the distal end is located in the peritoneal structure at the abdomen. The wall structure generally includes a biocompatible elastomer material, such as silicone, and an occlusion resistant material at one or both of the proximal and distal ends. In addition to or alternatively, the distal end may have different material properties than the proximal end in order to optimize the resistance to both occlusion and/or infection.

BRIEF DESCRIPTION OF THE DRAWINGS

FIG. 2 is a schematic of a shunt catheter tip demonstrating drug coating on inside and outside wall of catheter.

FIG. 3 is a schematic of a shunt catheter tip using drug-coated spheres.

FIG. 6 is a schematic of inserts which contain occlusion resisting materials surrounding the apertures of a catheter tip.

FIG. 7 is a close perspective of an insert of FIG. 6.

FIG. 8 through 13 are cross-sectional views of various locations of occlusion resistant materials on a shunt catheter.

FIG. 14 is a graph of drug release data from a catheter prepared by varying solvent and drug concentration.

DETAILED DESCRIPTION OF THE INVENTION

Figure 1:
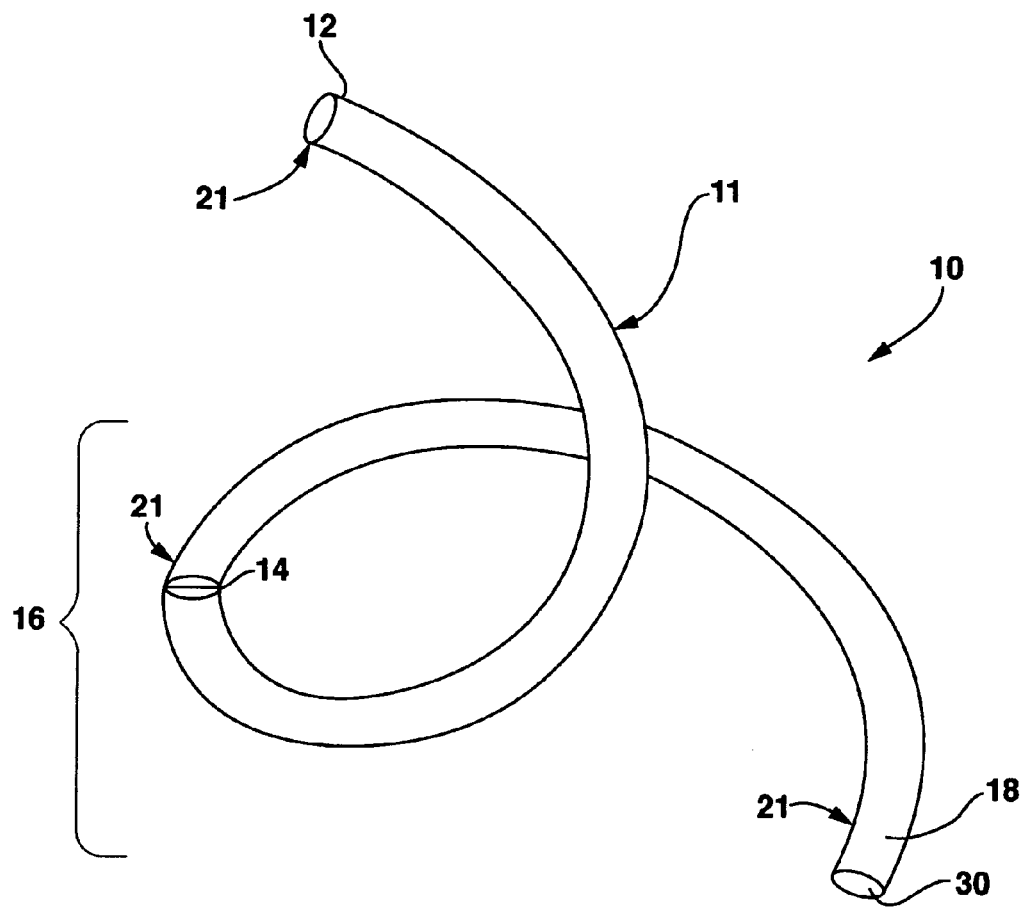
FIG. 1 is a schematic view of a shunt catheter.

Shunts for treatment of hydrocephalus are well known and have evolved over many decades. Although many cases of obstructive hydrocephalus are treated successfully with endoscopic fenestration of the floor of the third ventricles, there are also many types of hydrocephalus and hydrocephalic patients which require shunting. Typically, a hydrocephalic shunt includes a tubing with a proximal end located in the brain tissue and a distal end located either within the patient at another location external to the brain or external of the patient altogether. Such shunts also typically include a valve structure designed to accommodate flow based on the intracranial pressure and the position of the patient, i.e., configured for proper flow regulation when the patient is laying down versus standing up.

It is important to recognize that hydrocephalus is a condition, rather than a disease. Therefore, no two hydrocephalic patients are exactly like. In the past, however, hydrocephalic shunts have not fully recognized this important aspect of this condition, and therefore have not been customized to the degree possible under the present invention. Each patient must be considered for many variables that may affect the design and functionality of their hydrocephalic shunt. The age of the patient, the ventricular configuration, and the various compositions of cerebral spinal fluid will likely affect the considerations involved in the type of shunt design that is optimal for the patient. For example, the younger the patient, the smaller the brain ventricles. Also, for the younger patients the intracranial pressure is typically lower. Therefore, it is quite impossible to achieve a shunt which matches the needs of an infant with that of an adult. In similar fashion, each patient may experience a different allergic reaction or immune reaction to introduction of a shunt material. The above examples are provided to illustrate how complicated patients are who experience hydrocephalus and some of the considerations for optimizing treatment.

One of the most frequent hydrocephalus shunt complications is a shunt obstruction which occurs in approximately 50% of a pediatric series of shunts. In particular, the risk for shunt obstruction varies during the follow-up period but seems to be the highest in the immediate post-operative phase. In one analysis, the risk of obstruction was about 7 percent in the first post-operative month, and then dropped to 2 to 4 percent for the following four months. After the fifth month, the probability of such a complication was less than 0.5 percent per month for the next ten years. Different reasons for shunt obstruction can be expected during the immediate post-operative periods versus the following months. Cellular debris or a blood clot in the cerebrospinal fluid or misplacement of the proximal catheter is considered one cause of the early occlusions, whereas choroid plexus ingrowth, ependymal reaction or an immune reaction may predominate in delayed occlusions. Shunts have not been designed to address these known problems.

A shunt may be occluded at three different locations. First, at an entry point such as the proximal location in the brain, second, at the level of the valve system, commonly referred to as a "valve obstruction", and third, at the level of the distal end, referred to as a distal catheter occlusion. The focus of this invention relates to either distal or proximal occlusions rather than valve obstructions, although valve obstructions may be a sequelae of occlusions or infection migrating from the distal or proximal ends.

Proximal occlusions are more common than distal occlusions, and often result from blood or cellular debris which block the lumen and distal holes on ventricular catheters. This growth may depend on artificial properties (chemistry and geometry) as well as the distance between catheter and tissues in the ventricular (catheter positioning and slit ventricles syndrome). Some ventricular catheter tip designs have been proposed for maintaining the holes of the ventricular catheter away from the walls of the ventricles and the choroids plexus in order to resolve this problem. However, these devices are likely unable to fully prevent proximal occlusion from occurring. Moreover, those known as flanged catheters actually promote firm attachment of the catheter tubing to the choroids plexus. Although distal obstructions are not as frequent as that at the proximal end, shunt-type catheters can be obstructed in the peritoneal cavity by ingrowth of mesothelial cells and fibroblasts.

The inventors have recognized this phenomenon and have developed solutions which go beyond that currently known or suggested. FIG. 1 shows one embodiment of the hydrocephalic or CSF shunt 10 of the present invention, wherein the shunt 10 includes an elongated conduit 11 having a proximal portion 12, one or more valves 14, a central portion 16, and a distal portion 18. The elongated conduit 11 may be of any shape or size, but generally will be in the form of a tube made of an elastomeric material. As noted above, proximal portion 12 is placed in the patient's head at the region of the ventricles while the central portion 16 is routed subcutaneously along the patient's neck and torso. The distal portion 18 may be placed for drainage of the cerebral spinal fluid into the peritoneal cavity where the fluid is then reabsorbed by the normal bodily processes or may extend out of the patients body for external drainage.

It is evident that the proximal and distal portions 12,18 reside in different bodily environments, with different challenges to functionality. In the brain, where the majority of occlusion occurs, there ought to be different design considerations for proximal portion 12 than distal portion 18. However, proper recognition of this has not occurred in the past.

Accordingly, various embodiments of the present invention have included a hydrocephalic shunt 10 with a proximally located occlusion resistant or anti-occlusion agent 20, such as a drug or pharmaceutical, to locally interrupt the proliferation and inflammation processes. An example of such a shunt is depicted in FIGS. 2-10.

The inclusion of an occlusion resistant agent 20 positioned in or on the surface of the shunt 10 in drug eluting regions 21, such as the proximal portion 12, distal portion 18 and/or valve portion 14, permits the agent 20 to better manage the rate of failure of the shunt 10. Generally, the drug eluting regions 21 are portions of the shunt 10 wherein clotting or tissue growth tend to occlude the lumen of the shunt. In various embodiments of the present invention, the capability of an agent 20 located generally at a proximal portion 12 to reduce the failure of shunts due to occlusion may be achieved with one or more agents 20 selected from multiple classes. Such classes include anti-inflammatory drugs, immuno-suppressive drugs, anti-cancer drugs, anti-proliferatives, anti-migratories, anti-angiogenic drugs, radioactive or radiation-emitting material. Such classes may further include anti-neoplastics, anti-coagulents, anti-thrombogenics, anti-oxidants, cyclooxygenase inhibitors, calcium entry blockers, anti-neoplastics, anti-mitotics, anti-microbials, nitric oxide donors, cell cycle inhibitors, anti-arthritis agents, anti-diabetic agents, thrombin inhibitors, thrombolytics, antibiotics, antiviral agents, anti-proliferatives, anti-thrombogenics, anti-oxidants, cyclooxygenase inhibitors, calcium entry blockers, anti-mitotics, antimicrobials, nitric oxide donors, cell cycle inhibitors, anticancer agents, and gene therapy agents.

The following classes of anti-occlusion agents with examples in each class are possible embodiments of the occlusion resistant material for the invention. For example classes of anti-occlusion agents that may be utilized in embodiments of the present invention include immunosuppressives, anti-inflammatories, anti-neoplastics, anti-angiogenics, anti-coagulants, analgesics, antipyretics, anti-proliferatives, anti-thrombogenics, anti-oxidants, cyclooxygenase inhibitors, calcium entry blockers, anti-neoplastics, anti-mitotics, anti-microbials, antifungals, nitric oxide donors, cell cycle inhibitors, anti-cancer agents, anti-arthritis agents, anti-diabetic agents, thrombin inhibitors, thrombolytics, antibiotics, antiviral agents, and gene therapy agents. The following list provides additional examples of anti-occlusion agents that may be utilized in the present invention.

Anti-inflammatory—cortisone, hydrocortisone, prednisone, dexamethasone, methylprednisolone and their derivatives.

Non-steroidal anti-inflammatory agents including their racemic mixtures or individual enantiomers where applicable—ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antineoplastic/antiangiogenic—antimetabolite agents, alkylating agents, cytotoxic antibiotics, vinca alkaloids, mitosis inhibitors, platinum compounds, tissue growth factor inhibitors, cisplatin and etoposide Immunosuppressant agents—cyclosporine A, mycophenolic acid, tacrolimus, rapamycin, rapamycin analogue (ABT-578) produced by Abbott Laboratories, azathioprine, recombinant or monoclonal antibodies to interleukins, T-cells, B-cells and/or their receptors.

Antithrombogenic Factors—Anticoagulents, such as heparin and chondroiten sulfate; Platelet inhibitors such as ticlopidine; Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; and Thrombolytic agents, such as stretokinase, urokinase and tissue plasminogin activators.

Antiproliferative agents—paclitaxel, actinomycin D, rapamycin, tacrolimus, everolimus, dexamethasone and rapamycin analogue (ABT-578) produced by Abbott Laboratories;

Analgesics and antipyretics—the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Antimicrobials—the cephalosporins such as cephalexin, cefoxytin and cephalothin;

Antifungals—amorolfine, isoconazole, clotrimazole, econazole, miconazole, nystatin, terbinafine, bifonazole, amphotericin, griseo fulvin, ketoconazole, fluconazole and flucytosine, salicylic acid, fezatione, ticlatone, tolnaftate, triacetin, zinc, pyrithione and sodium pyrithione;

Antiviral agents—acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Local anaesthetics—benzocaine, bupivacaine, amethocaine, lignocaine, lidocaine, cocaine, cinchocaine, dibucaine, mepivacaine, prilocalne, etidocaine, veratridine (specific c-fiber blocker) and procaine;

Other miscellaneous antibiotics—chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Other pharmaceutical agents—beta-radiation emitting isotopes, beclomethasone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin, analogs, homologs, and derivatives of the above group.

The agent 20 may be applied by a variety of suitable application methods, such as a dip-coating techniques, spray coating techniques or as an impregnation of the agents 20 into the material utilized to produce the shunt walls. Additionally, the anti-occlusion agents 20 may be included in other carrier materials (not shown) that allow for the release of the agents 20, such as polymeric coatings. Once the anti-occlusion agents 20 are included in the carrier materials they may be applied to the shunts of the present invention utilizing the techniques disclosed above (i.e. dip coating, spray coating, etc.). The polymers utilized in the present invention can be bioabsorbable polmers, biostable polymers or combinations thereof. Suitable bioabsorbable polymeric coatings that may be utilized in embodiments of the present invention include, but are not limited to, poly(L-lactic acid), poly(lactide-co-glycolide) and poly(hydroxybutyrate-co-valerate). Suitable biostable polymers include, but are not limited to, silicones, polyurethanes, polyesters, vinyl homopolymers and copolymers, acrylate homopolymers and copolymers, polyethers, polyethylene, polypropylene, polycarbonate, polysulfone and cellulosics. Other polymers that may be utilized in embodiments of the present invention include polydimethylsiloxanes, methylhydrosiloxane-dimethylsiloxane copolymers, polymethylhydrosiloxanes, polyethylhydrosiloxanes, hydride terminated polyphenyl-(dimethylhydrosiloxy)siloxanes, methylhydrosiloxane-phenylmethylsiloxane copolymers, N-vinylpyrrolidone/methyl methacrylate copolymers, 2-hydroxyethylacrylate (e.g. polymacon), various copolymers of 2-hydroxyethylmethacrylate (e.g. hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.), polyamides, polyimides, fluoropolymers, polytetrafluoroethylenes, natural rubber and polyisoprene.

Other embodiments of the present invention provide a cannula utilized in medical applications, such as a shunt 10, that includes an agent delivery device 23, such as spheres, cloth, inserts, eluting plugs, seeds, elongated members or other similar structures positioned in the drug eluting regions 21. Various embodiments that include one or more agent delivery devices 23 are depicted in FIGS. 8-13 and will be further explained below. The feature of matching the right agent 20 to the right drug eluting region 21 to prevent or mitigate CSF shunt occlusion is beneficial to the optimum function of the shunt 10. Although the above discussion specifically mentioned the proximal portion 12, it is recognized by the inventors that these or similar agents may be used at the distal portion 18 as well, and at other selected locations if necessary. Additionally, embodiments of the shunt 10 of the present invention may utilized different agents 20 at different drug eluting regions 21. For example, a shunt 10 may include an anti-inflammatory medicament at the proximal tip 22 for placement within the brain tissue, a anticoagulant medicament at the valve portion 14 and an immunosuppressant medicament at the distal portion 18 for placement in the peritoneal region.

FIG. 2 depicts a cross sectional view of a portion of a CSF shunt 10 having a proximal portion 12 with a proximal tip 22 having a plurality of apertures 24 formed by a wall structure 26 of a catheter material such as a silicone or other similar biocompatible material. At least one internal lumen 28 is formed for guiding flow of cerebral spinal fluid from the proximal portion 12 through the shunt 10 and discharging the fluid from the distal portion 18 at distal tip 30 as depicted in FIGS. 1 and/or 2. To prevent occlusion of the shunt 10 there is provided one or more anti-occlusion agents 20 coated on either an external surface 32 of the proximal portion 12 or an internal lumenal surface 34. Again, each of these embodiments may also be employed at the shunt distal tip 30, or selectively at other sites.

Figure 4:
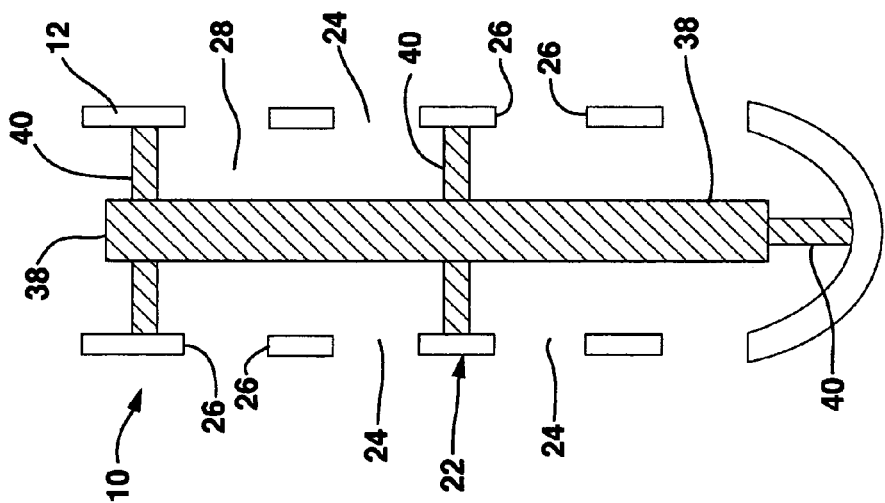
FIG. 4 is a schematic of a shunt catheter tip holding a radioactive core or seed.

Additionally, FIG. 3 depicts another embodiment of the present invention wherein a portion of an alternate design of shunt 10 having a plurality of hollow spheres 36 coated with a cytotoxic material, such as selenium, or impregnated with a low level beta emitting radioactive source material, such as 32P, 35S, 90Sr, 90Y. It is recognized that other types of radiation may be useful. Spheres are normally positioned in the lumen or embedded in the walls of the shunt. Spheres may be made of any suitable biocompatible material, such as glass, ceramic, metal, polymeric material or a combination thereof. The radioactive material may be utilized to inhibit the growth of tissue or formation of clotting in the openings and/or lumen or the shunt. Also, the radioactive or other material may be utilized in imaging techniques, such as MRI, Nuclear Medicine or Infrared, to identify irregularities in the shunt caused by tissue growth or clotting. FIG. 4 depicts another embodiment of the shunts of the present invention wherein a similar technical use of a radioactive source material is utilized, but configured as an elongated member 38, such as a rod or seed, centered by supports 40, or other means to stabilize and maintain the member 38 in the proximal portion 12 of the shunt 10.

Figure 5:
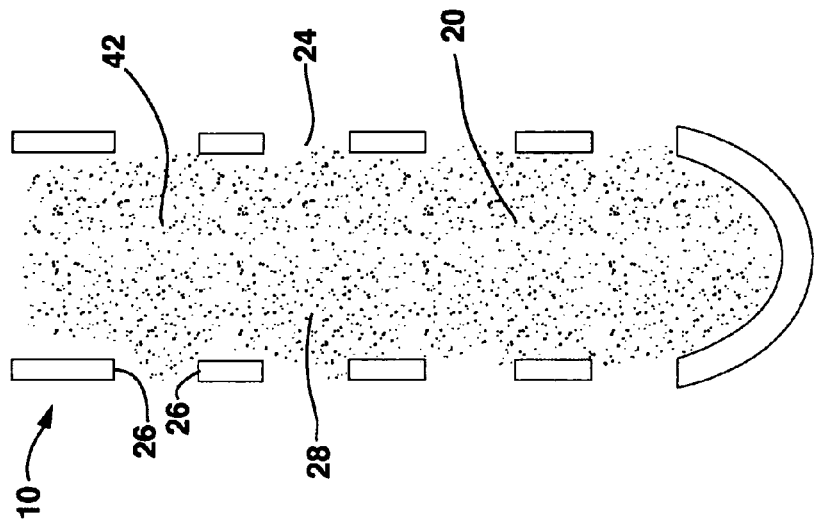
FIG. 5 is a schematic of a shunt catheter tip with a cloth-like insert impregnated with a occlusion resistant material.

FIG. 5 is a section view of a proximal portion 12 of a CSF shunt 10 in which a pliable material 42 such as a cloth, fabric or membrane material is included in the lumen 28. The pliable material or foam 42 may be coated or loaded with an agent 20, such as dexamethasone or sirolimus, for delivery from the shunt 10. The pliable material 42 may be selected from any suitable material, such as a polyethylene terephthalate fabric, an expanded poly(tetrafluoroethylene) material, porous polypropylene fibers, porous polyurethane, porous silicone, or any other polymer or polymeric foam, or various combinations of these materials. It is recognized that other porous inert and biostable substrates and methods suitable for immobilizing an elutable occlusion-preventing agent may be used.

FIG. 6 depicts a sectional view of another embodiment of the present invention wherein the proximal portion 12 of a CSF shunt 10 includes a plurality of inserts 44 adjoined to or incorporated into the wall structure 26 and adjacent to the apertures 24 of the proximal portion 12. The inserts may be integral to the wall structure or may be caps or plugs that interact with the wall structure ends near the apertures 24. Inserts 44 may be formed of any suitable material, such as a silicone rubber or other material and may be either coated or loaded with a radioactive or pharmaceutical agent 20, for example selenium or dexamethasone. This configuration focuses the occlusion preventing characteristics of the shunt 10 to the precise locations most affected. FIG. 7 is a perspective view of one embodiment of an insert 44. The inserts 44 may be made into any form that facilitates its interaction with the shunt 10, such as in the form of CSF permeable caps, disks, tabs, tubes, cylinders, or plugs. It is again noted that the embodiments depicted in FIGS. 3-6 may be utilized at the proximal or distal portions 12, 18 of the shunt or selectively at other sites of the shunt.

FIGS. 8-13 are sectional views of further embodiments of proximal portions 12 of the present invention including one or more anti-occlusion agents 20 loaded onto or into the shunt 10. As previously mentioned in other embodiments, other portions of the shunt 10 depicted in FIGS. 8-13, such as the distal portion 18 or valve portion 14 may also include such drugs or anti-occlusion agents 20. FIG. 8 depicts one embodiment of a proximal portion 12 of shunt 10 the wall structures 26 include fluid apertures 24 and a closed tip 46. Within closed tip 46 there is positioned a plug 48 comprising a material having occlusion preventing characteristics, such as the inclusion of pharmaceutical agents 20. In one embodiment of the present invention, a dexamethasone plug is provided, as further described in examples below.

Plugs 48 utilized in embodiments of the present invention may be prepared utilizing a variety of techniques, such as extrusion or molding techniques. For example, in one embodiment of the present invention a plug is prepared by mixing a polymer, such as silcone, with an anti-occlusion agent, such as rapamycin or MPA. The polymer/agent mixture is then administered or injected into selective positions in the wall structure 26, valve portion, proximal tip 22, distal tip 30 or other location wherein occlusion of the shunt 10 generally originates and is allowed to set. In another embodiment agent delivery devices 23, such as plugs, seeds, caps or inserts, may be formed by extruding the polymer/agent mixture through an extrusion device or administering the polymer/agent mixture to a mold and allowing polymerization of the mixture to form the agent delivery device 23. Once formed by the extrusion or molding technique, the agent delivery device 23 may be adjoined to the elongated conduit 11 at one or more drug eluting regions 21 utilizing any securing means, such as solvent welding, adhesives, form fitting or by any other technique that will adequately secure the agent delivery device 23 to the shunt 10.

FIG. 9 depicts another embodiment of the shunt of the present invention, which includes a drug eluting coating 50 of a drug eluting material, such as a polymeric material, to provide localized effect of the occlusion-preventing pharmaceutical agent 20 within the coating 50. FIG. 10 discloses another embodiment in which a tablet 52 of a drug eluting material is placed within closed tip 46. FIG. 11 also uses drug eluting seeds 52, but placing one or more in the wall material 26 rather than fully embedded within the closed tip 46. It is noted that the plugs, seeds and coatings may include one or more anti-occlusion agents 20 formulated into the seed or coating or may include the one or more anti-occlusion agents 20 intermingled with one or more bioabsorbable or biostable polymer, which carry the anti-occlusion agents 20. Suitable bioabsorbable polymeric coatings that may be utilized in embodiments of the present invention include, but are not limited to, poly(L-lactic acid), poly(lactide-co-glycolide) and poly(hydroxybutyrate-co-valerate). Suitable biostable polymers include the biostable polymers listed above, (e.g. silicones, polyurethanes, polyesters, vinyl homopolymers and copolymers, acrylate homopolymers and copolymers, polyethers, polyamides, polyimides, fluoropolymers, polytetrafluoroethylenes, natural rubber and polyisoprene and cellulosics).

FIG. 12 illustrates a drug loading using an impregnation approach. In one embodiment of the present invention the pharmaceutical agent 20 is dissolved in an organic solvent. Suitable organic solvents that may be utilized in the present application include, but are not limited to water, alcohols such as ethanol, methylene chloride, Xylene, Hexane, Acetone, Dimethyl Sulfoxide (DMSO), Tetrahydrofuran (THF) or combinations thereof. The amount of anti-occlusion agent added to the solvent is generally about 0.001 wt % to approximately 30 wt %, preferably about 0.05 wt % to about 5 wt % of the mixture. Next, the wall material 26 is immersed in the pharmaceutical saturated solvent thereby swelling and loading the material with pharmaceutical saturated solvent. As shown in FIG. 12, only the portion of the shunt tubing which was immersed into the drug solution will be impregnated with drugs thereby forming the drug loaded tube portion 54.

FIG. 13 depicts another example of drug distribution in a shunt 10, wherein an elastomeric material, such as silicone, and drug mixture is extruded to form a shunt 10. In contrast to an impregnation approach, shown in FIG. 12, an extrusion approach as depicted in FIG. 13 may provide an optimum distribution of drug along the length of the extruded tubing. In such an embodiment the elastomeric material/drug mixture may include an amount of occlusion resistant agent, which is approximately 0.00001 wt % to about 20 wt %, preferably from about 0.001 wt % to about 1 wt % of the mixture. Once formed the elastomer/drug mixture may be extruded utilizing any extrusion device known in the art. It is recognized, however, that within the extrusion art it is possible to selectively configure extrusion steps and apparatus to further optimize by layer or location the drug distribution (or elution) rate, loading, and other characteristics.

Applicants have identified the value of having a CSF shunt proximal tip 22 with a first concentration of a drug 24 to interfere with tissue occlusion of the shunt 10 and a distal tip 30 having either no drug/agent, having the same drug/agent, or having a different concentration or a different drug/agent than the proximal tip 22. Also, a combination of agents 24 may be appropriate to protect patentcy of the shunt lumen 28 during the acute and chronic phases of the shunt implant. Combinations of drugs may also demonstrate different elution rates to achieve synergistic therapeutic outcomes not found or even expected otherwise. This, again, is a new approach to providing CSF shunts which are adapted to the specific needs, tolerances, and conditions of each patient. For example, it may be more desirable to use an anti-inflammatory agent A1 as a slow and focused eluting seed in a proximal tip, which also has less neuro-toxicity than agent A2—which may be impregnated in a wider area of the distal tip wall material.

In addition to using or combining one or more drugs/agents onto different portions of a shunt catheter, it is possible to combine more than one class of drug as well. For example, pharmaceutical agents within the various classes described herein may comprise one or more of the agents on or within a CSF shunt 10.

In operation, the drainage shunt 10 may be partially implanted in the head of a patient. More specifically, the shunt 10 may be positioned with its proximal portion 12 positioned near the brain of patient to allow for drainage of cerebrospinal fluid, "water", from the area of the brain. The positioning of the shunt 10 is intended to relieve a hydrocephalic condition. Additionally, the flow of fluid to the distal portion 18 from the proximal end 12 of the shunt 10 may be controlled by a valve 14 positioned between the proximal and distal portions 12, 18. For normal operation of the drainage shunt 10, the proximal portion 12 is connected to valve 14 to establish fluid communication between the ventricle region of the brain to other areas, such as the peritoneal cavity or out of the body altogether. For example, this connection may allow for the transfer of water from the area of brain to the chest area or abdomen area of the patient. The proper operation of the shunt 10, however, requires that the lumen 28 of shunt 10 remain patent.

As can be easily appreciated, the patency of the shunt lumen 28 is compromised whenever the proximal or distal tips 22, 30 of shunt 10 become clogged or occluded. For example, this condition may happen if the proximal tip 22 of shunt 10 is inadvertently placed too near the choroid plexus of brain. Should this happen, it is possible the choroid plexus may grow into the lumen 28 through the proximal tip 22 and thereby disrupt the drainage of water from brain through the shunt 10. However, as previously suggested in the above mentioned embodiments, this condition may be avoided by inclusion of one or more anti-occlusion agents 20 in the drug eluting regions 21 of the shunt 10.

EXAMPLES

The following examples teach how to load drugs into different portions of a hydrocephalus shunt, including, for example, the ventricular and peritoneal portions of a hydrocephalic shunt 102 using different techniques. Four model drugs are used throughout these examples to illustrate the effect of the drug's physical properties: dexamethasone phosphate (hydrophilic drug), dexamethasone free base (more hydrophobic than dexamethasone phosphate), dexamethasone acetate (most hydrophobic), and mycophenolic acid. By changing the method of drug loading, one skilled in the art can adjust drug release, as shown by drug releasing profiles used in the examples below.

Example 1

Drug Loaded Using an Impregnation Approach

Standard shunt ventricular catheter silicone tubing (translucent, OD=0.083", ID=0.048"), made of platinum cured silicone rubber (Silastic MDX4-4210, Medical grade), was inserted into glass beakers containing solutions of Dexamethasone-acetate (DEX-Ac) in mixture, as specified in Table 1.

TABLE 1

DEX-Ac loading of 20 mg weight pieces of shunts were made by placing each in 1 g of the solution, composition of which is given in this table.

| Sample | wt % DEX-AC | Xylene:Acetone |
|--------|-------------|----------------|
| 2 | 0.86 | 9:1 wt/wt |
| 3 | 6.45 | 1:3 wt/wt |
| 4 | 4.3 | 1:1 wt/wt |

Samples were incubated at 40° C. for 18.5 h, following by rinsing with Xylene and drying in a vacuum oven for 28 h. Samples were positioned in glass vials with a fixed amount of PBS buffer. Release test was done at 37° C. in a 0.01 M PBS buffer containing 0.138M NaCl and 0.0027M KCl using an incubator shaker (model C24 from New Brunswick Scientific Inc.), which was set up at 100 RPM. Drug release amount was estimated by UV-VIS test, performed at 240 nm using 1 cm optical length quarts cuvette. Drug release kinetics are shown in FIG. 14, with profile 151 correlating to Sample 2, and Samples 3 and 4 represented by Profiles 153, 154.

Tetrahydrofuran (THF) was used to obtain 200 volume % swelling of silicone rubber. Because most of the hydrophobic drugs are soluble in THF, this solvent can be an excellent candidate for loading hydrophobic drugs by swelling approach.

Example 2

Drug loading using a Dip-coating Approach

Figure 15:
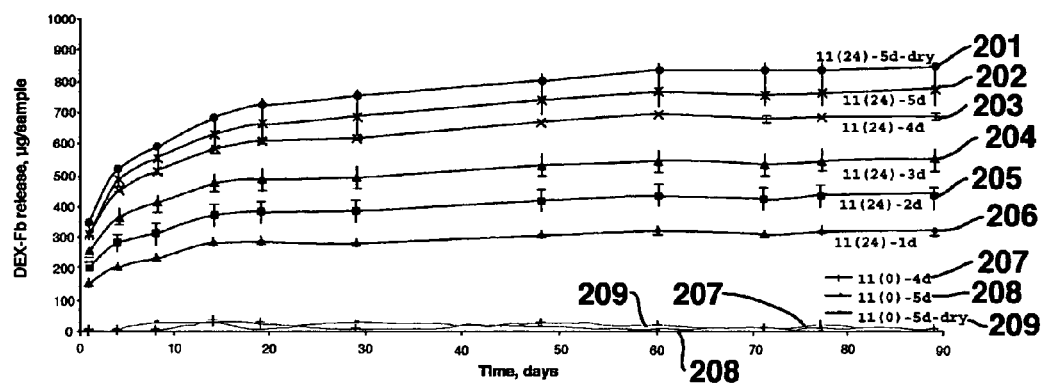
FIG. 15 is a graph of drug release data from a catheter prepared by a dip-coating method.

RTV Silicone glue (MED 1137, Nusil), and Dexamethasone free base (DEX-Fb, UpJohn S7185) free base were dissolved in tetrahydrofuran (THF) to achieve final concentrations of solids which were measured in PBS buffer. A distal part of the silicone catheter was dipped into this solution using a withdrawal speed of either 1.0 cm/s or 0.2 cm/s, different drying periods, differing numbers of dipping, and with different release profiles. After solvent evaporation and silicone curing, samples were analyzed for dexamethasone release. Release profiles are shown in FIG. 15, with profiles illustrating DEX-Fb release in micrograms/sample over days. Profiles 201, 202, 203, 204, 205, 206, 207, 208, and 209 represent total percent of solids in THF (percent of DEX in solids)—number of dip coatings. For example, Profile 203 is 11(24)-4d, and this represents a sample which was dip coated four times with a THF solution containing 11 weight percent of solids (i.e., DEX-Fb and RTV-silicone) and 24 weight percent of DEX-Fb of total solids weight. The term "-dry" represents samples having a longer drying period between dipping steps.

Example 3

Barrier Coating Slows Down the Drug Release.

Samples, coated as described in the above Example 2 were additionally dipped into pure RTV silicone solution in THF (11 wt %) to form a barrier layer. These additional coatings resulted in a four fold decrease of an initial burst of the released dexamethasone.

Example 4

Multiple Dip-Process Modifies a Drug Release Profile

The procedure described in the above Example 2 was repeated two, three, four and five times with an intermediate drying time in between the dip coating steps of 5 to 30 min. Dexamethasone loading onto shunt determined by the sample weight change after dipping procedure increased five times after five step dipping, while the dexamethasone release rate increased less than three times after five step dipping.

Example 5

Solvent Free Technologies for Drug Loading Into Shunt.

The raw ingredients of platinum cured silicone rubber (silastic MDX4-4210, Medical grade, Batch 0-000617734) were mixed with either dexamethasone free base (Fb, UpJohn S7185) or dexamethasone phosphate (Ph, UpJohn 12CCA) or the mixture of two drugs together at total drug concentration from 20 wt % to 50 wt %. Ingredients were added into a mixing container and were well mixed using Speed mixer DAC 150FV. Total mixing time (from 20 sec to 80 sec) and a mixer frequency (from 1800 rpm to 3300 rpm) were adjusted to obtain the homogeneous mixture as verified by visual observation and low magnification optical microscopy. Silicone tubing was filled with this mixture using the proper size of syringe. It was done either manually or with an automated air dispenser system. Size of plug was visually controlled to be in a range of 3-4 mm.

Figure 16:
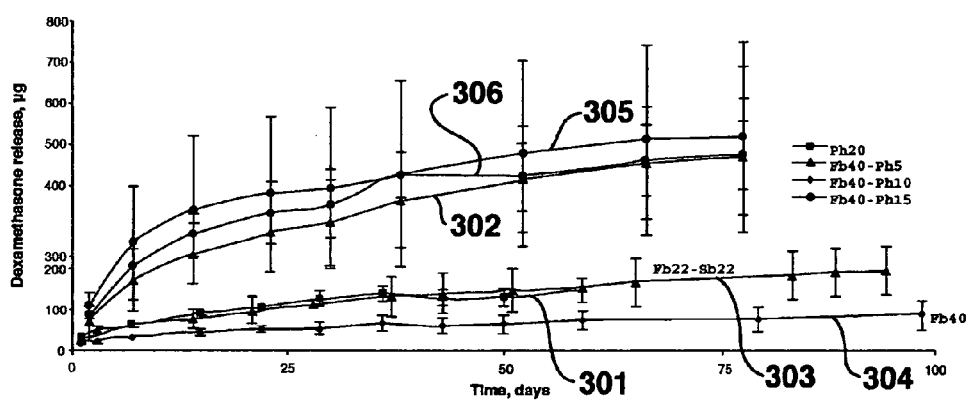
FIG. 16 is a graph of drug release data from a catheter prepared by a barrier layer method.

Plugged tubes were cured at 150° C. for 2 h followed by a weekend at room temperature. Drug release was measured as described in the above Example 1. The release profiles are given in FIG. 16. In FIG. 16, the sample abbreviation Ph20 at Profile 301 means that dexamethasone phosphate was mixed with silicone rubber at 20 wt % concentration of drug. Sample abbreviation Fb40-Ph5 at Profile 302 means that dexamethasone free base and dexamethasone phosphate were mixed with silicone rubber at concentrations of 40 wt % and 5 wt %, respectively. Sample abbreviation Fb22-Sb22 at Profile 303 means that dexamethasone free base and sodium bicarbonate were mixed with silicone rubber at concentrations of 22 wt % and 22 wt %, respectively. Profiles 304, 305, and 306 correspond using similar labeling methodology.

Example 6

Additives Modulate Drug Release Profile

Figure 17:
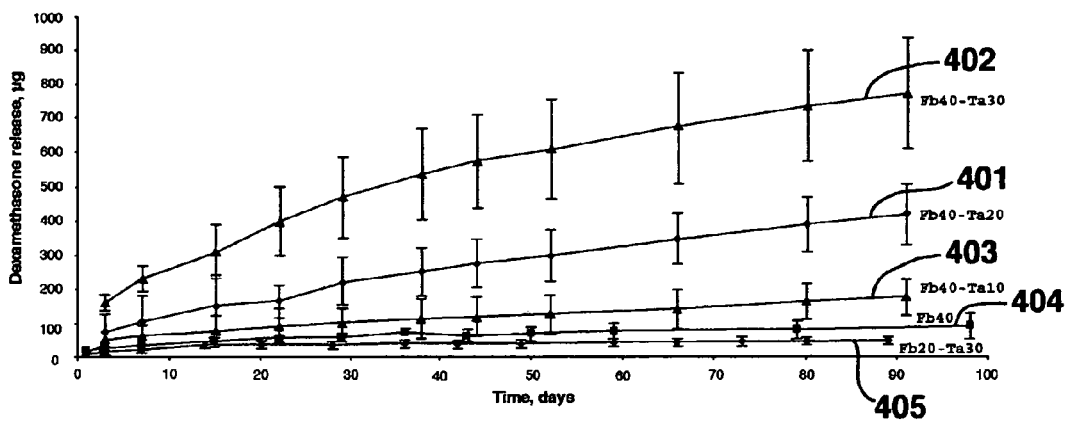
FIG. 17 is a graph of drug release data from a catheter with additive modulated methods.

Sodium bicarbonate (Sb, Aldrich, pre-sieved to control the salt granule size) at concentration of 22 wt % or Tantalum powder (Ta, Aldrich) at concentrations between 10 wt % and 30 wt % were added to silicone/drug mixtures, described in the above Example 5, to modulate the dexamethasone release from the samples. Drug release was measured as described in Example 1. The release profiles are given in FIG. 16 (curve Fb22-Sb22, Profile 303) and FIG. 17. In FIG. 17, the sample abbreviation Fb40-Ta20 at Profile 401 means that dexamethasone free base and tantalum powder were mixed with silicone rubber at concentrations of 40 wt % and 20 wt %, respectively. Profiles 402, 403, 404 and 405 are labeled using similar methodology.

Example 7

Drug Loading By an Extrusion Process

Figure 18:
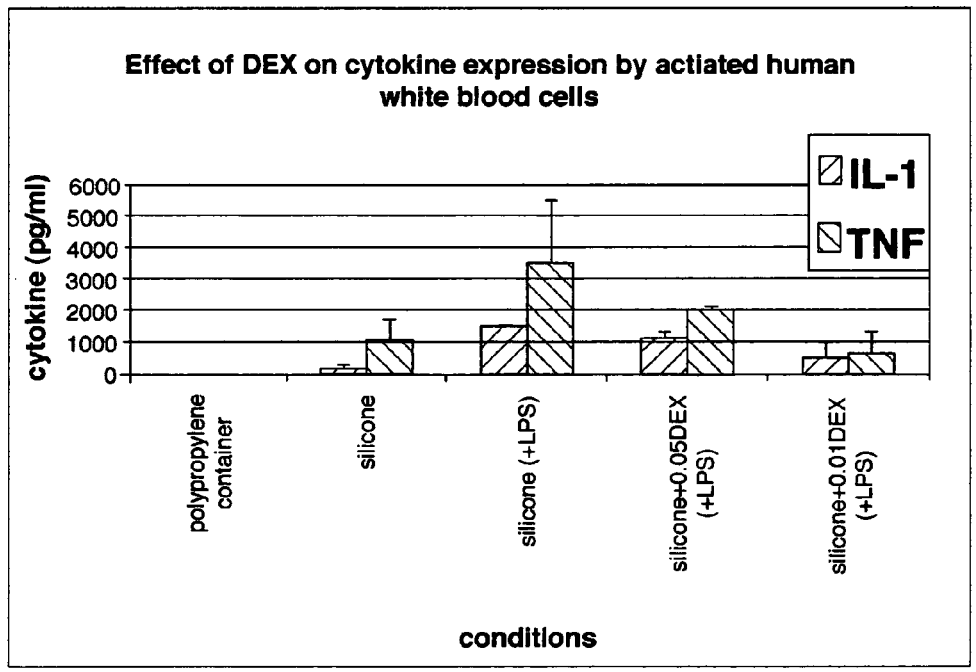
FIG. 18 is a graph of drug release data from a catheter prepared with drug loading by extrusion process and shows cytokine release from activated from human cells in the presence of silicon and several dexamethasone concentrations.

Dexamethasone free base was mixed at concentrations from 0.05 wt % to 0.1 wt % with raw ingredients of platinum cured rubber (Silastic MDX4-4210, Medical grade). The tubing (OD=2.1 mm; ID-1.1 mm) was extruded and cured according to a standard procedure, which involves a short-term (seconds) silicone/drug exposure to the elevated temperatures of around 200° C. during the extrusion process. The drug released from this sample remained active after extrusion, as indicated in FIG. 18 by the effect of the presence of the sample in the tubing with activated white blood cells. In this Figure, the effect of released dexamethasone from the extruded tubing on two potential inflammatory cytokines (IL-1a, TNF-a) is shown. In this case LPS, a bacterial endotoxin, is added to the white blood cells to cause them to release the cytokines. 0.1 DEX corresponds to samples made by adding 0.1 wt % of dexamethasone to silicone rubber. 0.05DEX corresponds to samples made by adding 0.05 wt % of dexamethasone to silicone rubber. Both dexamethasone release samples had anti-inflammatory effects in this in-vitro assay.

Example 8

Immunosuppressive agent's Effect On a Neuronal Cell Line

Figure 19:
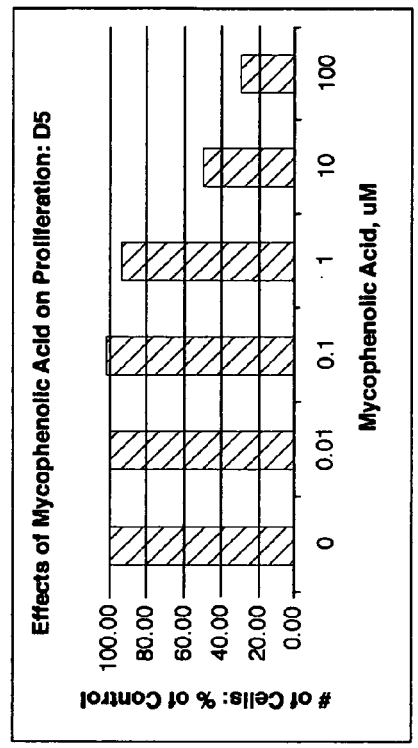
FIG. 19 is a graph of drug release data from an immunosuppressant.
Figure 20:
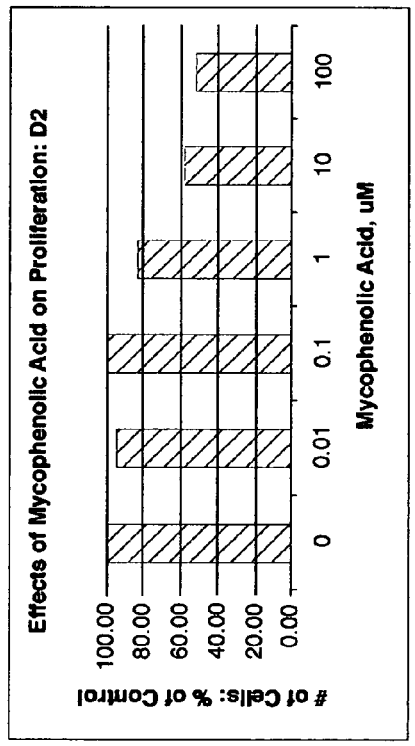
FIG. 20 is a graph of drug release data from an immunosuppressant.

Cells were seeded at 20,000 cells per well at Day 0 with mycophenolic acid (MPA) at six different concentrations. Cells were counted using an ATP/luciferase assay at Day 2 (as shown in FIG. 19) and Day 5 (as shown in FIG. 20). The ratios of cell counts are shown as percent of cell numbers in the wells with MPA compared to cell numbers in wells without MPA.

Example 9

Anti-proliferative agent's Effect On a Neuronal Cell Line

Figure 21:
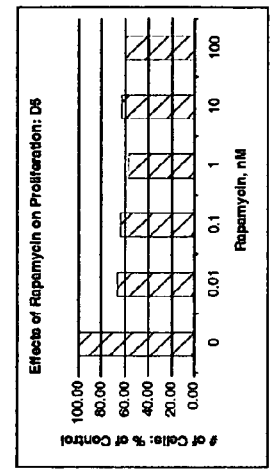
FIG. 21 is a graph of drug release data from an antiproliferative.
Figure 22:
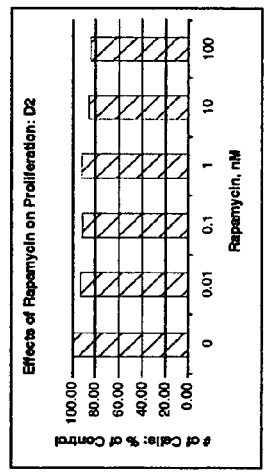
FIG. 22 is a graph of drug release data from an antiproliferative.

Cells were seeded at 20,000 cells per well at Day 0 with Rapamycin (RAPA) at six different concentrations. Cells were counted using an ATP/luciferase assay at Day 2 (as shown in FIG. 21) and Day 5 (as shown in FIG. 22). The ratios of cell counts are shown as percent of cell numbers in the wells with RAPA compared to cell numbers in wells without RAPA.

Example 10

Anti-neoplastic Agent's Effect On a Brain-derived Cell Line

Figure 24:
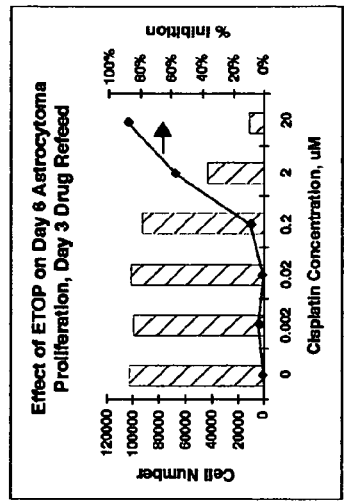
FIG. 24 is a graph of drug release data from an antineoplastic.
Figure 23:
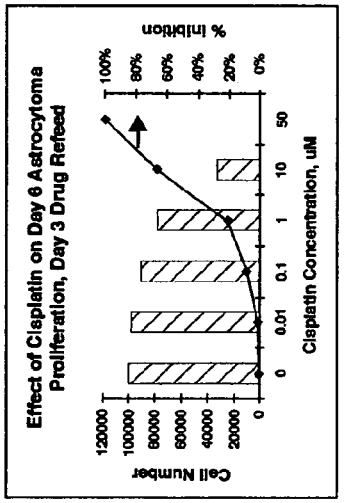
FIG. 23 is a graph of drug release data from an antineoplastic.

Cells were seeded at 20,000 cells per well at Day 0 with Cisplatin (FIG. 23) and Etoposide (FIG. 24) at six different concentrations. Cells were counted using an ATP/luciferase assay at Day 3. FIGS. 23 and 24 show the effect of Cisplatin and Etoposide on Day 6 Astrocytoma proliferation with a Day 3 refeed.

Example 11

Immunosuppressive Agent's Release From Medical Catheter

Figure 25:
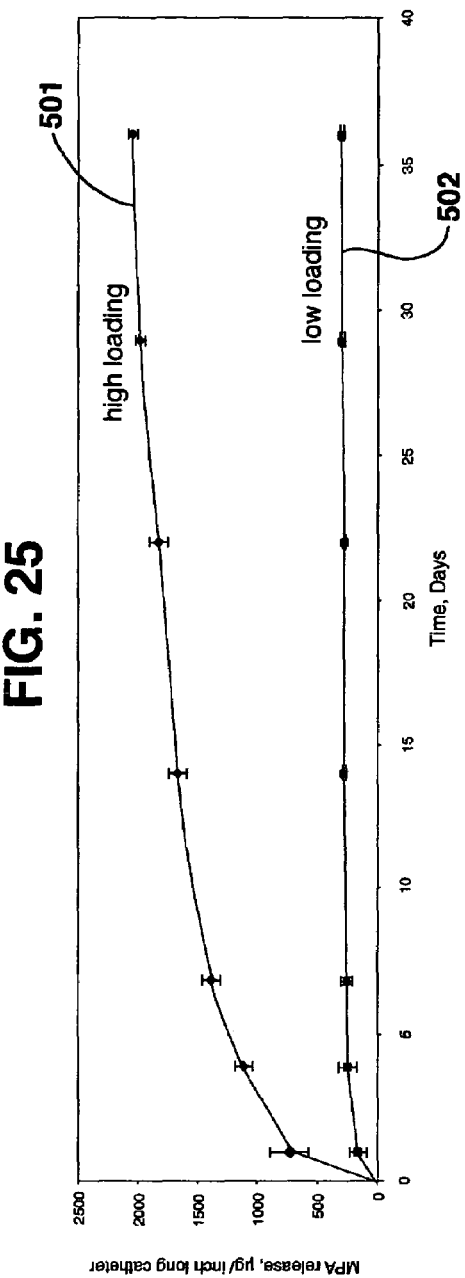
FIG. 25 is a graph of drug release data from an immunosuppressant in a catheter.

Mycophenolic acid (MPA) release is achieved from a silicone catheter into PRS buffer using an impregnation approach with results as shown in FIG. 25. Impregnation occurred by soaking silicone catheters for ten minutes at room temperature with 5.0 mg/ml (high loading) at Profile 501 and 0.5 mg/ml (low loading) at Profile 502 solutions of MPA in tetrahydrofuran. High and low loading catheters had initial MPA content of 2.520±0.12 mg and 0.30±0.04 mg respectively.

Example 12

MPA Release from Shunt

Figure 26:
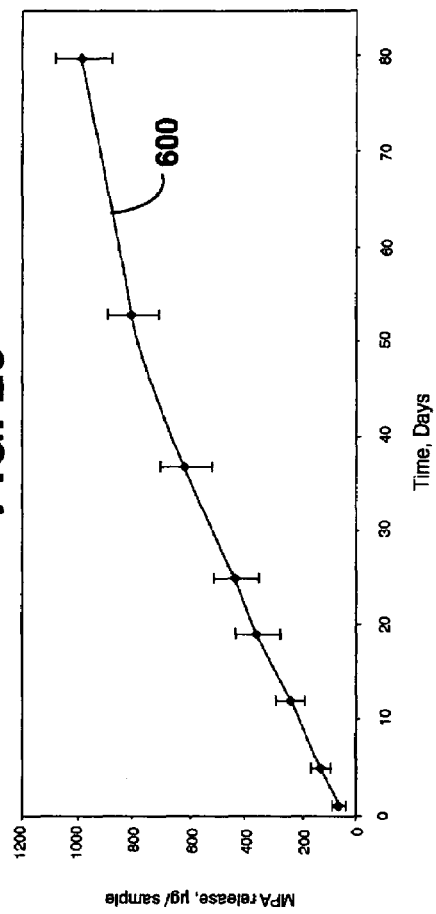
FIG. 26 is a graph of drug release data from an immunosuppressant in a shunt.

Mycophenolic acid was loaded in a silicone shunt by placing the distal part of the shunt in a 5 mg/ml solution of MPA in THF for 30 minutes at room temperature. After drying at room temperature for 24 hours, the samples were dip-coated with 11 wt % of RTV silicone in THF to form a barrier layer which reduces initial drug release. MPA release is shown at Profile 600 in a buffer in FIG. 26.

Example 13

Immunosuppressive Agent's Release From Catheter Using Dip-coating

Figure 27:
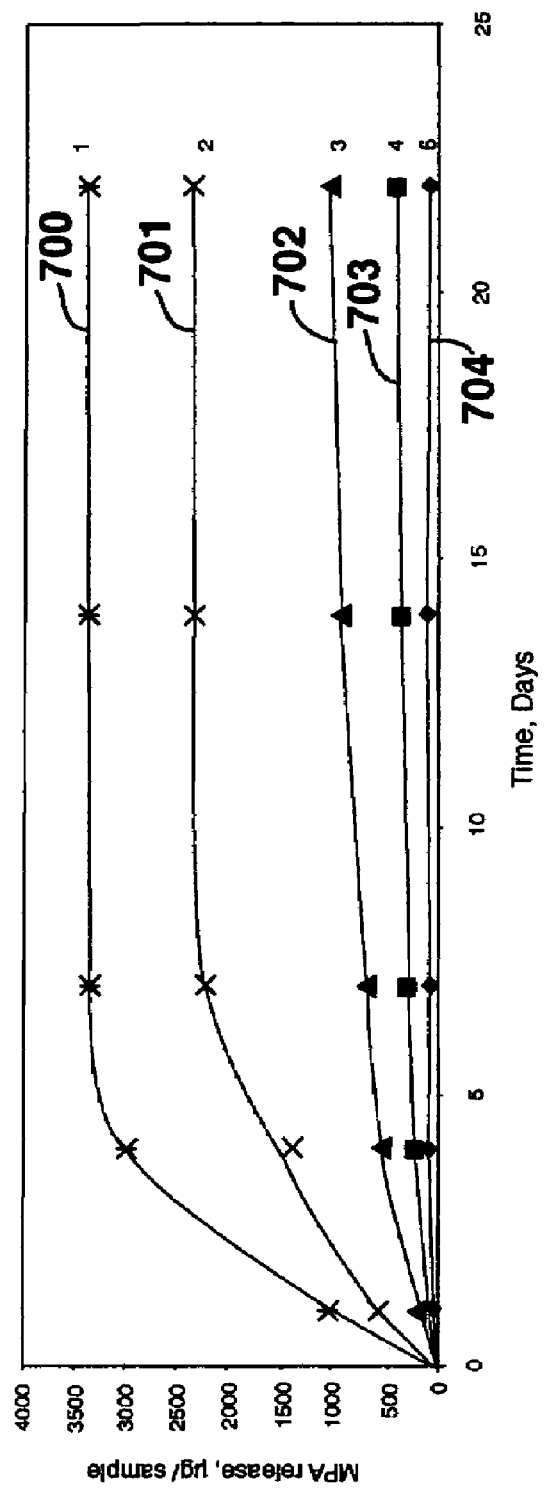
FIG. 27 is a graph of drug release data from an immunosuppressant in a catheter.

MPA release from a silicone catheter dip coated into a PRS buffer is seen in FIG. 27. Profiles 700, 701, 702, 703 and 704 designate the following dipping conditions, respectively: 33 Wt. % of MPA in solids; 20 Wt. % of MPA in solids; 10 Wt. % of MPA in solids; 5.0 Wt. % of MPA; 1.0 Wt. %. Total solids concentrations is 10 Wt. % in tetrahydrofuran dipping solution.

Example 14

Immunosuppressive Agent's Release from a Catheter Using a Silicone Plug

Figure 28:
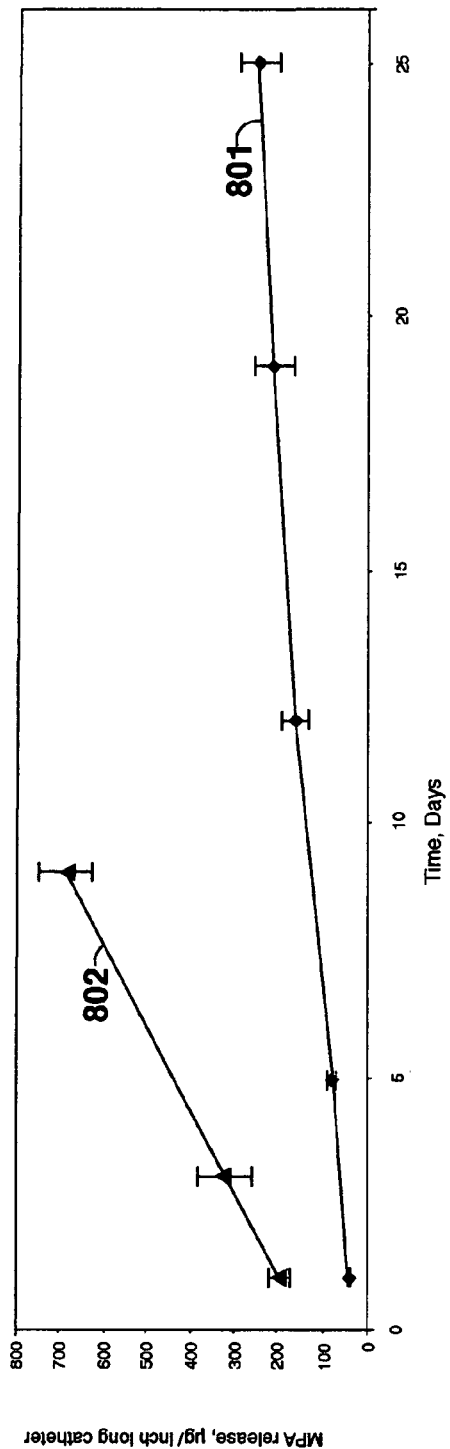
FIG. 28 is a graph of drug release data from an immunosuppressant in a catheter.

MPA release from silicone plugs into PRS buffer is seen in FIG. 28. Profiles 801, 802 designate the following plug conditions, respectively: 10 wt. % MPA, 90% wt. % platinum cured rubber; 10 wt. % MPA, 30 wt. % sodium bicarbonate and 60 wt. % platinum cured rubber. Initial MPA loadings were 2.34 mg±0.15 mg and 3.40 mg±0.11 mg for Profiles 801, 802, respectively.

Example 15

Anti-proliferative Agent's Loading Into a Shunt by Impregnation Followed by Drug Loading Into a Shunt Plug Rapamycin (RAPA) was loaded into a shunt by an impregnation process, according to which a distal part of a silicone shunt was placed in a 1 mg/ml solution of RAPA in THF for 30 minutes followed by drying at room temperature for 24 hours. Plugs were then made in a shunt using a platinum cured rubber, containing 0.1 wt % RAPA. These shunts were cleaned, packaged and ETO sterilized. Samples were then placed in a cell media for 4 hours. This media was added to an Astrocytoma cell culture, which resulted in a two fold inhibition of the cell growth, as compared to a fresh media.

Example 16

RAPA Release From a Shunt

Figure 29:
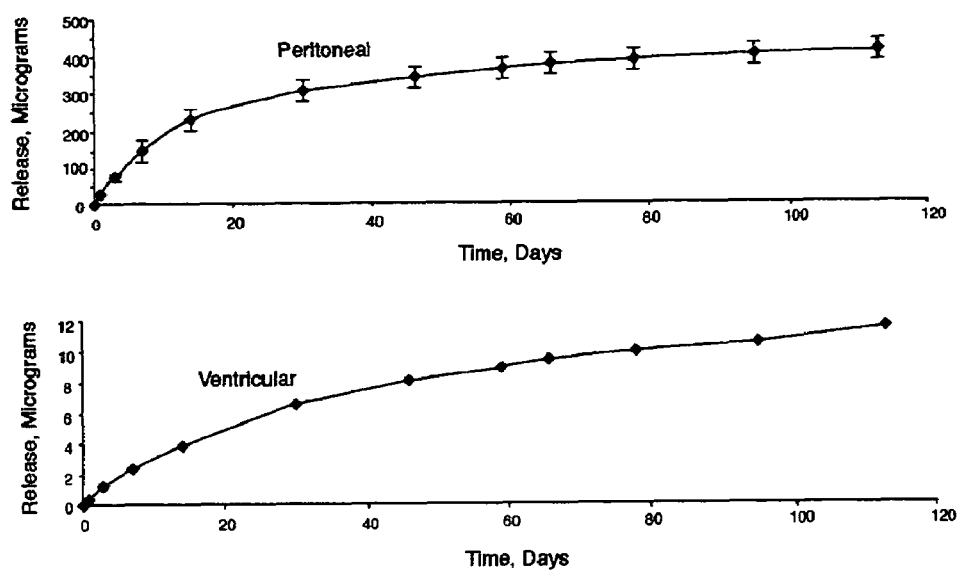
FIG. 29 is a graph of drug release data from an immunosuppressant in a catheter with a silicone plug.

Rapamycin (also named sirolimus) was loaded into a standard shunt catheter (called further peritoneal catheter) and into a downsized catheter (called further ventricular catheter). Ventricular catheters were 6 mm long with 2 mm silicone plug and 16 laser drilled holes. OD and ID of ventricular catheters were 0.30 mm and 0.65 mm respectively. Hole diameter was 0.30 mm. Peritoneal catheters were 15 mm long with 3 mm silicone plug and 28 hand punched holes. OD and ID of peritoneal samples were 2.09 mm and 1.21 mm, respectively. Hole diameter was 0.61 mm. Both catheters were made of 9% barium filled silicone rubber. Drug loading was done according to the following procedure: silicone tubing pieces were impregnated with RAPA solution in tetrahydrofuran (downsized: 100 mg/mL; standard: 20 mg/mL). Drug releasing plugs, comprised of RAPA and platinum cured silicone rubber (5 wt % RAPA), were injected into one end of each tubing piece. RTV silicone rubber caps were placed on the distal end of each piece (i.e. over the end of the plug) to direct most of drug release into a catheter lumen. All samples were ethylene oxide sterilized prior measurement of drug release. In-vitro drug release was done in PBS buffer at 37° C. using a mild shaking. Drug concentration was determined by UV-VIS measurements. As can be seen from FIG. 29, long-term release rate were achieved using disclosed drug loading approaches.

Example 17

In-vivo Proof of the Efficacy of a Single Drug Release for Mitigation of Tissue Proliferation Micophenolic acid (MPA) was loaded into ventricular and peritoneal catheter, design of which is described in the example 16. MPA was loaded into ventricular catheter by solvent impregnation using 50 mg/ml MPA in THF followed by drug loading into a silicone plug with 10 wt % drug concentration. Peritoneal sample was loaded by solvent impregnation using 12.5 mg/ml MPA solution in THF followed by drug loading into a plug using 2.5 mg/ml MPA in silicone rubber. Samples were implanted into rat such that the ventricular sample was placed in a lateral ventricle of the rat and the peritoneal samples was implanted into rat peritoneal cavity. In total 6 ventricular and 6 peritoneal samples were implanted into 6 rats. 12 drug-free catheters of the same configuration were implanted in the other 6 rats as controls. After 3 months samples were explanted and the tissue in-growth was scored between 1 and 5 on a basis of SEM photographs of longitudinally split catheters. Results are presented in Table 1. Here a score of 1 represents 0 to 10% tissue coverage of the lumen; a 2 is for 10% to 25% coverage; a 3 is for 25% to 50% coverage; 4 is for 50% to 75% coverage and a 5 is for 75% to 100% coverage. As can be seen from Table 1, local drug release of MPA resulted in decrease of tissue proliferation for both peritoneal and ventricular catheters.

Example 18

In-vivo Proof of the Efficacy of a Dual-drug Release for Mitigation of Tissue Proliferation Ventricular and peritoneal samples were loaded with RAPA and MPA according to the following procedure: catheters were impregnated with 50 mg/ml of MPA solution in THF followed by plugging with 5 wt % RAPA in silicone Samples were implanted in rats and analyzed as described in the Example 17. Results are given in Table 1. Dual drug loading led to a stronger inhibition of the tissue proliferation if compared to a single drug loading.

TABLE 1

Tissue in-growth scores for MPA loaded and control samples.

|  | Drug free control | MPA loaded | MPA and RAPA loaded |
| --- | --- | --- | --- |
| peritoneal | 4.03 ± 0.38 | 2.75 ± 0.53 | 2.20 ± 0.45 |
| ventricular | 3.03 ± 0.61 | 2.17 ± 0.51 | 1.48 ± 0.41 |

It was found that the combined release of drugs, as measured in-vitro after 2 months, was 30 micrograms for the ventricular catheter and 1080 micrograms for the peritoneal catheter.

Thus, embodiments of the occlusion resistant hydrocephalic shunt are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An occlusion resistant medical shunt for at least partial implantation into a patient, said shunt comprising an elongated conduit having a lumen therethrough, a proximal end for receipt of bodily fluids for flow through said shunt and a distal end for discharge of said bodily fluids from said shunt, a plurality of apertures at the proximal end of said shunt, said shunt further including one or more occlusion-resistant materials distributed in one or more separate agent delivery device (s) contained within the lumen of said shunt;
   wherein said agent delivery device is not coated on, or impregnated in, the shunt wall, and
   wherein said agent delivery device(s) is selected from the group consisting of spheres, inserts, eluting plugs, seeds, elongated members and combinations thereof, and
   wherein the one or more occlusion-resistant materials are released internally from said agent delivery devices to resist occlusion of the lumen of the shunt.

2. The occlusion resistant medical shunt of claim 1 wherein the shunt further includes at least one valve.

3. The occlusion resistant medical shunt of claim 1 wherein the elongated conduit includes one or more elastomeric materials selected from the group consisting of poly(L-lactic acid), poly(lactide-co-glycolide), poly(hydroxybutyrate-co-valerate), silicones, polyurethanes, polyesters, vinyl homopolymers and copolymers, acrylate homopolymers and copolymers, polyethers, polyethylene, polypropylene, polycarbonate, polysulfone, cellulosics, polydimethylsiloxanes, methylhydrosiloxane-dimethylsiloxane copolymers, polymethylhydrosiloxanes, polyethylhydrosiloxanes, hydride terminated polyphenyl-(dimethylhydrosiloxy)siloxanes, methylhydrosiloxane-phenylmethylsiloxane copolymers, N-vinylpyrrolidone/methyl methacrylate copolymers, 2-hydroxyethylacrylate (e.g. polymacon), various copolymers of 2-hydroxyethylmethacrylate (e.g. hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.), polyamides, polyimides, fluoropolymers, polytetrafluoroethylenes, natural rubber and polyisoprene.

4. The occlusion resistant medical shunt of claim 1 wherein the elongated conduit comprises a silicone elastomer material.

5. The occlusion resistant medical shunt of claim 1 wherein the elongated conduit comprises polyurethane material.

6. The occlusion resistant medical shunt of claim 1 wherein the occlusion-resistant material includes a material selected from the group of agents consisting of immunosuppressives, anti-inflammatories, anti-neoplastics, radiation emitting materials, anti-angiogenics, anti-coagulants, anti-proliferatives, anti-thrombogenics, anti-oxidants, cyclooxygenase inhibitors, calcium entry blockers, anti-neoplastics, anti-mitotics, anti-mierobials, nitric oxide donors, cell cycle inhibitors, anti-cancer agents, anti-arthritis agents, anti-diabetic agents, thrombin inhibitors, thrombolytics, antibiotics, antiviral agents, and gene therapy agents.

7. The occlusion resistant medical shunt of claim 6 wherein the occlusion-resistant material includes a material selected from the group consisting of beta-radiation emitting isotopes, dexamethasone, beclomethasone, cortisone, hydrocortisone, prednisone, methylprednisone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, paclitaxel, etoposide, actinomycin D, camptothecin, carmustine, methotrexate, adriamycin, mitomycin, cisplatinum, mitosis inhibitors, vinca alkaloids, tissue growth factor inhibitors, platinum compounds, cytotoxic inhibitors, alkylating agents, antimetabolite agents, tacrolimus, rapamycin, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin, rapamycin ABT-578 and analogs, homologs, derivatives or combinations of the above group.

8. The occlusion resistant shunt of claim 7 wherein the occlusion resistant material includes a material selected from the group consisting of mycophenolic acid, rapamycin, rapamycin ABT-578, derivatives or combinations thereof.

9. The occlusion resistant shunt of claim 7 wherein the occlusion resistant material includes mycophenolic acid.

10. The occlusion resistant shunt of claim 7 wherein the occlusion resistant material includes a combination of mycophenolic acid and, rapamycin or rapamycin ABT-578.

11. The occlusion resistant medical shunt of claim 1 wherein the occlusion-resistant material is distributed uniformly throughout the shunt.

12. The occlusion resistant medical shunt of claim 1 wherein the occlusion-resistant material is distributed only in drug eluting regions.

13. The occlusion resistant medical shunt of claim 12 wherein different occlusion-resistant materials are used in different drug eluting regions of the shunt.

14. The occlusion resistant medical shunt of claim 1 wherein the occlusion-resistant material is distributed non-uniformly throughout the shunt and in different amounts.

15. The occlusion resistant medical shunt of claim 14 wherein the occlusion-resistant material is released at different rates between different portions of the shunt.

16. An occlusion resistant medical cannula for at least partial implantation into a patient, said cannula comprising an elongated conduit having a lumen therethrough, a proximal end for receipt of bodily fluids for flow through said cannula and a distal end for discharge of said bodily fluids from said cannula, a plurality of apertures at the proximal end of said cannula, said cannula further including one or more occlusion-resistant materials distributed in one or more separate agent delivery device(s) that is not coated on or impregnated in the shunt wall and is contained within the lumen of said cannula, wherein said agent delivery device(s) is selected from the group consisting of spheres, inserts, eluting plugs, seeds, elongated members and combinations thereof, wherein the one or more occlusion-resistant materials are released internally from one or more agent delivery devices that provide occlusion resistance of the lumen of the cannula.

17. The occlusion resistant medical cannula of claim 16 wherein the cannula further includes at least one valve.

18. The occlusion resistant medical cannula of claim 16 wherein the elongated conduit includes one or more elastomeric materials selected from the group consisting of poly(L-lactic acid), poly(lactide-co-glycolide), poly(hydroxybutyrate-co-valerate), silicones, polyurethanes, polyesters, vinyl homopolymers and copolymers, acrylate homopolymers and copolymers, polyethers, polyethylene, polypropylene, polycarbonate, polysulfone, cellulosics, polydimethylsiloxanes, methylhydrosiloxane-dimethylsiloxane copolymers, polymethylhydrosiloxanes, polyethylhydrosiloxanes, hydride terminated polyphenyl-(dimethylhydrosiloxy)siloxanes, methylhydrosiloxane-phenylmethylsiloxane copolymers, N-vinylpyrrolidone/methyl methacrylate copolymers, 2-hydroxyethylacrylate (e.g. polymacon), various copolymers of 2-hydroxyethylmethacrylate (e.g. hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.), polyamides, polyimides, fluoropolymers, polytetrafluoroethylenes, natural rubber and polyisoprene.

19. The occlusion resistant medical cannula of claim 18 wherein the elongated conduit comprises a silicone elastomer material.

20. The occlusion resistant medical cannula of claim 18 wherein the elongated conduit comprises polyurethane material.

21. The occlusion resistant medical cannula of claim 16 wherein the occlusion-resistant material includes a material selected from the group of agents consisting of immunosuppressives, anti-inflammatories, anti-neoplastics, anti-angiogenics, anti-coagulants, anti-proliferatives, anti-thrombogenics, anti-oxidants, cyclooxygenase inhibitors, calcium entry blockers, anti-neoplastics, anti-mitotics, anti-mierobials, nitric oxide donors, cell cycle inhibitors, anti-cancer agents, anti-arthritis agents, anti-diabetic agents, thrombin inhibitors, thrombolytics, antibiotics, antiviral agents, and gene therapy agents.

22. The occlusion resistant medical cannula of claim 21 wherein the occlusion-resistant material includes a material selected from the group consisting of beta-radiation emitting isotopes, dexamethasone, beclomethasone, cortisone, hydrocortisone, prednisone, methylprednisone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, paclitaxel, etoposide, actinomycn D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, rapamycin, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin, rapamycin ABT-578 and analogs, homologs, derivatives or combinations of the above group.

23. The occlusion resistant medical cannula of claim 22 wherein the occlusion resistant material includes a material selected from the group consisting of mycophenolic acid, rapamycin, rapamycin ABT-578, derivatives or combinations thereof.

24. The occlusion resistant shunt of claim 23 wherein the occlusion resistant material includes mycophenolic acid.

25. The occlusion resistant shunt of claim 23 wherein the occlusion resistant material is a combination of mycophenolic acid and rapamycin or rapamycin ABT-578.

26. The occlusion resistant medical cannula of claim 16 wherein different occlusion-resistant materials are used in different agent delivery devices included in the cannula.

27. The occlusion resistant medical cannula of claim 16 wherein the occlusion-resistant material is distributed non-uniformly throughout the agent delivery devices and in different amounts.

28. The occlusion resistant medical cannula of claim 27 wherein the occlusion-resistant material is released at different rates between different agent delivery devices of the cannula.

29. A method of preparing an occlusion resistant shunt comprising:
providing an elongated conduit having a lumen therethrough and including a proximal end for receipt of bodily fluids for flow through said shunt and a distal end for discharge of said bodily fluids from said shunt, said conduit having plurality of apertures at the proximal said shunt, administering to said shunt one or more occlusion-resistant materials distributed in one or more separate agent delivery devices that is not coated on, or impregnated in, the shunt wall and is contained within the lumen of said shunt, wherein said agent delivery device(s) is selected from the group consisting of spheres, inserts, eluting plugs, seeds, elongated members and combinations thereof, wherein the one or more occlusion-resistant materials are released internally from said agent delivery devices to resist occlusion of the lumen of said shunt.

30. The method of preparing an occlusion resistant shunt of claim 29 wherein the shunt further includes at least one valve.

31. The method of preparing an occlusion resistant shunt of claim 29 wherein the elongated conduit includes one or more elastomeric materials selected from the group consisting of poly(L-lactic acid), poly(lactide-co-glycolide), poly(hydroxybutyrate-co-valerate), silicones, polyurethanes, polyesters, vinyl homopolymers and copolymers, acrylate homopolymers and copolymers, polyethers, polyethylene, polypropylene, polycarbonate, polysulfone, cellulosics, polydimethylsiloxanes, methylhydrosiloxane-dimethylsiloxane copolymers, polymethylhydrosiloxanes, polyethylhydrosiloxanes, hydride terminated polyphenyl-(dimethylhydrosiloxy)siloxanes, methylhydrosiloxane-phenylmethylsiloxane copolymers, N-vinylpyrrolidone/methyl methacrylate copolymers, 2-hydroxyethylacrylate (e.g. polymacon), various copolymers of 2-hydroxyethyl-methacrylate (e.g. hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.), polyamides, polyimides, fluoropolymers, polytetrafluoroethylenes, natural rubber and polyisoprene.

32. The method of preparing an occlusion resistant shunt of claim 29 wherein the elongated conduit comprises a silicone elastomer material.

33. The method of preparing an occlusion resistant shunt of claim 29 wherein the elongated conduit comprises polyurethane material.

34. The method of preparing an occlusion resistant shunt of claim 29 wherein the occlusion-resistant material includes a material selected from the group of agents consisting of immunosuppressives, anti-inflammatories, anti-neoplastics, anti-angiogenics, anti-coagulants, anti-proliferatives, anti-thrombogenics, anti-oxidants, cyclooxygenase inhibitors, calcium entry blockers, anti-neoplastics, anti-mitotics, anti-microbials, nitric oxide donors, cell cycle inhibitors, anti-cancer agents, anti-arthritis agents, anti-diabetic agents, thrombin inhibitors, thrombolytics, antibiotics, antiviral agents, and gene therapy agents.

35. The method of preparing an occlusion resistant shunt of claim 34 wherein the occlusion-resistant material includes a material selected from the group consisting of beta-radiation emitting isotopes, dexamethasone, beclomethasone, cortisone, hydrocortisone, prednisone, methylprednisone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, paclitaxel, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, rapamycin, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin, rapamycin ABT-578 and analogs, homologs, derivatives or combinations of the above group.

36. The method of preparing an occlusion resistant shunt of claim 35 wherein the occlusion resistant material includes a material selected from the group consisting of mycophenolic acid, rapamycin, rapamycin ABT-578, derivatives or combinations thereof 37. The occlusion resistant shunt of claim 36 wherein the occlusion resistant material includes mycophenolic acid.

38. The occlusion resistant shunt of claim 32 wherein the occlusion resistant material includes a combination of mycophenolic acid and, rapamycin or rapamycin ABT-578.

39. The method of preparing an occlusion resistant shunt of claim 29 wherein the occlusion-resistant material is distributed uniformly throughout the shunt.

40. The method of preparing an occlusion resistant shunt of claim 29 wherein the occlusion-resistant material is distributed only in drug eluting regions.

41. The method of preparing an occlusion resistant shunt of claim 29 wherein the drug eluting regions are selected from the group consisting of the proximal portion, the distal portion, and one or more valves.

42. The method of preparing an occlusion resistant shunt of claim 41 wherein different occlusion-resistant materials are used in different drug eluting regions of the shunt.

43. The method of preparing an occlusion resistant shunt of claim 29 wherein the occlusion-resistant material is distributed non-uniformly throughout the shunt and in different amounts.

44. The method of preparing an occlusion resistant shunt of claim 43 wherein the occlusion-resistant material is released at different rates between different portions of the shunt.

45. A method of inhibiting the occlusion of an at least partially implanted shunt comprising:
implanting a shunt including an elongated conduit having a lumen therethrough, a proximal end for receipt of bodily fluids for flow through said shunt and a distal end for discharge of said bodily fluids from said shunt, said shunt having a plurality of apertures at the proximal of said shunt, said shunt further including one or more occlusion-resistant materials distributed in one or more separate agent delivery device(s) that is not coated on, or impregnated in, the shunt wall and is contained within the lumen of said shunt, wherein said agent delivery device(s) is selected from the group consisting of spheres, inserts, eluting plugs, seeds, elongated members, and combinations thereof; and releasing from said agent delivery devices the one or more occlusion-resistant materials to inhibit the occlusion of the lumen of said shunt.

46. The method of inhibiting the occlusion of an at least partially implanted shunt of claim 45 wherein the shunt further includes at least one valve.

47. The method of inhibiting the occlusion of an at least partially implanted shunt of claim 45 wherein the elongated conduit includes one or more elastomeric materials selected from the group consisting of poly(L-lactic acid), poly(lactide-co-glycolide), poly(hydroxybutyrate-co-valerate), silicones, polyurethanes, polyesters, vinyl homopolymers and copolymers, acrylate homopolymers and copolymers, polyethers, polyethylene, polypropylene, polycarbonate, polysulfone, cellulosics, polydimethylsiloxanes, methylhydrosiloxane-dimethylsiloxane copolymers, polymethylhydrosiloxanes, polyethylhydrosiloxanes, hydride terminated polyphenyl-(dimethylhydrosiloxy)siloxanes, methylhydrosiloxane-phenylmethylsiloxane copolymers, N-vinylpyrrolidone/methyl methacrylate copolymers, 2-hydroxyethylacrylate (e.g. polymacon), various copolymers of 2-hydroxyethylmethacrylate (e.g. hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.), polyamides, polyimides, fluoropolymers, polytetrafluoroethylenes, natural rubber and polyisoprene.

48. The method of inhibiting the occlusion of an at least partially implanted shunt of claim 45 wherein the elongated conduit comprises a silicone elastomer material.

49. The method of inhibiting the occlusion of an at least partially implanted shunt of claim 45 wherein the elongated conduit comprises polyurethane material.

50. The method of inhibiting the occlusion of an at least partially implanted shunt of claim 45 wherein the occlusion-resistant material is selected from the group of agents consisting of immunosuppressives, anti-inflammatories, anti-neoplastics, anti-angiogenics, anti-coagulants, anti-proliferatives, anti-thrombogenics, anti-oxidants, cyclooxygenase inhibitors, calcium entry blockers, anti-neoplastics, anti-mitotics, anti-microbials, nitric oxide donors, cell cycle inhibitors, anti-cancer agents, anti-arthritis agents, anti-diabetic agents, thrombin inhibitors, thrombolytics, antibiotics, antiviral agents, and gene therapy agents.

51. The method of inhibiting the occlusion of an at least partially implanted shunt of claim 50 wherein the occlusion-resistant material includes a material selected from the group consisting of beta-radiation emitting isotopes, dexamethasone, beclomethasone, cortisone, hydrocortisone, prednisone, methylprednisone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, paclitaxel, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, rapamycin, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin, rapamycin ABT-578 and analogs, homologs, derivatives or combinations of the above group.

52. The method of inhibiting the occlusion of an at least partially implanted shunt of claim 51 wherein the occlusion resistant material includes a material selected from the group consisting of mycophenolic acid, rapamycin, rapamycin ABT-578, derivatives or combinations thereof 53. The occlusion resistant shunt of claim 52 wherein the occlusion resistant material includes mycophenolic acid.

54. The occlusion resistant shunt of claim 46 wherein the occlusion resistant material includes a combination of mycophenolic acid and, rapamycin or rapamycin ABT-578.

55. The method of inhibiting the occlusion of an at least partially implanted shunt of claim 45 wherein the occlusion-resistant material is distributed uniformly throughout the shunt.

56. The method of inhibiting the occlusion of an at least partially implanted shunt of claim 45 wherein the occlusion-resistant material is distributed only in drug eluting regions.

57. The method of inhibiting the occlusion of an at least partially implanted shunt of claim 45wherein the drug eluting regions are selected from the group consisting of the proximal portion, the distal portion, and one or more valves.

58. The method of inhibiting the occlusion of an at least partially implanted shunt of claim 57 wherein different occlusion-resistant materials are used in different drug eluting regions of the shunt.

59. The method of inhibiting the occlusion of an at least partially implanted shunt of claim 45 wherein the occlusion-resistant material is distributed non-uniformly throughout the shunt and in different amounts.

60. The method of inhibiting the occlusion of an at least partially implanted shunt of claim 59 wherein the occlusion-resistant material is released at different rates between different portions of the shunt.

* * * * *

UNITED STATES PATENT AND TRADEMARK OFFICE
CERTIFICATE OF CORRECTION

PATENT NO. : 7,582,068 B2  Page 1 of 1
APPLICATION NO. : 10/781568
DATED : September 1, 2009
INVENTOR(S) : Koullick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,582,068 B2  Page 1 of 1
APPLICATION NO. : 10/781568
DATED : September 1, 2009
INVENTOR(S) : Edouard Koullick, Marc Hendriks and William Bertrand It is certified that error appears in the above-identified patent and that said Letters Patent is hereby corrected as shown below:

Pat. Col. 17, Line 22, claim #6:
....anti-mierobials,.....   Should read as   ......anti-microbials,.....

Pat. Col. 18, Line 54, claim #21 (23):
....anti-mierobials.....   Should read as   ......anti-microbials......

Pat. Col. 18, Line 67, claim #22 (24):
......actinomycn.......   Should read as   ......actinomycin...........

Signed and Sealed this
Sixteenth Day of August, 2011

David J. Kappos
*Director of the United States Patent and Trademark Office*